United States Patent
Wang et al.

(10) Patent No.: US 10,891,730 B1
(45) Date of Patent: Jan. 12, 2021

(54) FIBER PATTERN REMOVAL AND IMAGE RECONSTRUCTION ENDOSCOPIC DEVICES AND RELATED METHODS

(71) Applicant: University of Southern California, Los Angeles, CA (US)

(72) Inventors: Pu Wang, Monterey Park, CA (US); Francesco Cutrale, San Gabriel, CA (US); Scott E. Fraser, Glendale, CA (US)

(73) Assignee: University of Southern California, Los Angeles, CA (US)

( * ) Notice: Subject to any disclaimer, the term of this patent is extended or adjusted under 35 U.S.C. 154(b) by 104 days.

(21) Appl. No.: 16/206,958

(22) Filed: Nov. 30, 2018

Related U.S. Application Data (60) Provisional application No. 62/593,079, filed on Nov. 30, 2017.

(51) Int. Cl.
*G06T 7/00* (2017.01)
*G06T 5/00* (2006.01)
*A61B 1/00* (2006.01)

(52) U.S. Cl.
CPC .......... *G06T 7/0012* (2013.01); *A61B 1/0017* (2013.01); *A61B 1/00167* (2013.01); *G06T 5/006* (2013.01)

(58) Field of Classification Search
CPC .................. G06T 5/006; G06T 7/0012; G06T 2207/10036; G06T 3/4007; A61B 1/00167; A61B 1/0017
See application file for complete search history.

(56) References Cited

U.S. PATENT DOCUMENTS

| 9,784,681 B2 * | 10/2017 | de Boer | G01J 3/0218 |
| 2008/0097225 A1 * | 4/2008 | Tearney | A61B 1/07 600/478 |
| 2009/0237498 A1 * | 9/2009 | Modell | H04N 17/002 348/65 |

(Continued)

OTHER PUBLICATIONS

S. Rupp, C. Winter and M. Elter, "Evaluation of spatial interpolation strategies for the removal of comb-structure in fiber-optic images," 2009 Annual International Conference of the IEEE Engineering in Medicine and Biology Society, Minneapolis, MN, 2009, pp. 3677-3680. (Year: 2009).*

(Continued)

*Primary Examiner* — Uptal D Shah
(74) *Attorney, Agent, or Firm* — Fish & Richardson P.C.

(57) ABSTRACT

Implementations of the present disclosure include methods, systems, and computer-readable storage mediums for image reconstruction. Actions include receiving an image acquired by an endoscopic system including an optical fiber bundle with multiple optical fibers, each optical fiber being surrounded by cladding, determining in the image fiber core locations corresponding to the optical fibers, reconstructing missing information from the image using interpolation performed in accordance with the fiber core locations, the missing information corresponding to artifacts in the acquired image that result from the cladding, and providing a fiber-pattern removed image, in which the artifacts in the acquired image are removed using the missing information.

20 Claims, 5 Drawing Sheets

(56) References Cited

U.S. PATENT DOCUMENTS

| | | | |
|---|---|---|---|
| 2011/0054252 A1* | 3/2011 | Ozaki | A61B 1/00089 |
| | | | 600/109 |
| 2014/0378845 A1* | 12/2014 | Nadkarni | A61B 5/6853 |
| | | | 600/478 |
| 2020/0069165 A1* | 3/2020 | Thomson | A61B 1/063 |

OTHER PUBLICATIONS

Stephan Rupp, "A quantitative performance measure for a clinical evaluation of comb structure removal algorithms in flexible endoscopy," Proc. SPIE 6914, Medical Imaging 2008: Image Processing, 69141C (Mar. 11, 2008) (Year: 2008).*

* cited by examiner

FIBER PATTERN REMOVAL AND IMAGE RECONSTRUCTION ENDOSCOPIC DEVICES AND RELATED METHODS

CROSS-REFERENCE TO RELATED APPLICATIONS

This application claims the benefit under Title 35 United States Code § 119(e) of U.S. Provisional Application No. 62/593,079 filed Nov. 30, 2017, which is hereby incorporated by reference.

STATEMENT AS TO FEDERALLY SPONSORED RESEARCH

This invention was made with government support under Contract No. PR150666 awarded by the U.S. Department of Defense (DoD). The government has certain rights in the invention.

TECHNICAL FIELD

This disclosure relates to endoscopic devices and related methods for pattern removal in images acquired using optical fiber bundles.

BACKGROUND

Recent technological advancements in detection sensors simplified the acquisition of hyperspectral imaging (HSI) data and bridged the gap between HSI and multiple applications in the biomedical field. HSI explores the spectral dimension to differentiate tissues apart based on their intrinsic optical properties. Many groups seek to take advantage of HSI and combine it with flexible endoscopes (FE). However, there is one issue with combining these two imaging modalities. The design of optical fiber bundles can be generalized as a multitude of fiber cores surrounded by cladding. One common artifact of this bundle approach is a comb pattern on the images, which complicates image analysis. Especially for HSI, it is complicated to directly and accurately implement spectral analysis if the image is divided by claddings.

SUMMARY

The present disclosure describes endoscopic devices and related methods for image reconstruction. Such image reconstruction can be used for removing image artifacts associated with optical fiber cladding.

In general, one or more aspects of the subject matter described in this specification can be embodied in a computer-implemented method executed using one or more processors, a non-transitory computer-readable storage medium coupled to one or more processors or a system including: an endoscopic system, a client-side computing device, and a computer-readable storage device coupled to the client-side computing device and having instructions stored thereon which, when executed by the client-side computing device, cause the client-side computing device to perform operations for image reconstruction. The operations include: receiving, by the one or more processors, an image acquired by an endoscopic system including an optical fiber bundle including a plurality of optical fibers, wherein each of the plurality of optical fibers is surrounded by cladding, determining, by the one or more processors, in the image a plurality of fiber core locations corresponding to the plurality of optical fibers in the optical fiber bundle, reconstructing, by the one or more processors, missing information from the image using interpolation performed in accordance with the plurality of fiber core locations, wherein the missing information corresponds to artifacts in the acquired image that result from the cladding, and providing, by the one or more processors, a fiber-pattern removed image in which the artifacts in the acquired image are removed using the missing information.

Embodiments may include one or more of the following features.

In some implementations, reconstructing the missing information includes: performing, by the one or more processors, Delaunay triangulation on the plurality of fiber core locations to generate triangulation data, and performing, by the one or more processors, Barycentric interpolation using the triangulation data to produce the missing information. Determining the plurality of fiber core locations in the image can include localizing fiber core pixels using a reference image and a two dimensional Gaussian function to model light coming out from each of the plurality of optical fibers. Determining the plurality of fiber core locations in the image can include: performing, by the one or more processors, a first round of fiber core pixel candidate screening using individual threshold values set in accordance with illumination settings of the endoscopic system, and performing, by the one or more processors, a second round of fiber core pixel candidate screening to remove incorrect core pixels.

In some implementations, performing the second round of fiber core pixel candidate screening includes using a mask-based approach to remove incorrect core pixels. In some implementations, the image includes a hyperspectral image, and the method includes performing, by the one or more processors, spectral correction for the fiber-pattern removed image. Performing the spectral correction can include: recovering same-bandwidth spectra, and correcting spectral distortions associated with the endoscopic system. Performing the spectral correction can include using a reshaped reflectance matrix. In some implementations, the operations of receiving, the determining, the reconstructing, and the providing are performed in semi-real time.

The details of one or more implementations of the subject matter of this specification are set forth in the Detailed Description, the Claims, and the accompanying drawings. Other features, aspects, and advantages of the subject matter will become apparent to those of ordinary skill in the art from the Detailed Description, the Claims, and the accompanying drawings.

DESCRIPTION OF DRAWINGS

FIGS. 3A-3J illustrate an example of a fiber pattern removal algorithm diagram in accordance with implementations of the present disclosure.

DETAILED DESCRIPTION

Like reference numbers and designations in the various drawings indicate like elements.

Implementations of the present disclosure are generally directed to a hyperspectral imaging system. More specifically, implementations of the present disclosure are directed to a fiber pattern removal algorithm designed for hyperspectral endoscopic imaging. Various modifications, alterations, and permutations of the disclosed implementations can be made and will be readily apparent to those of ordinary skill in the art, and the general principles defined can be applied to other implementations and applications, without departing from the scope of the present disclosure. In some instances, one or more technical details that are unnecessary to obtain an understanding of the described subject matter and that are within the skill of one of ordinary skill in the art may be omitted so as to not obscure one or more described implementations. The present disclosure is not intended to be limited to the described or illustrated implementations, but to be accorded the widest scope consistent with the described principles and features.

The techniques and systems described in the present disclosure can remove a fiber pattern from endoscopic images (e.g., RGB (true color) images and hyperspectral images) by using a two-step process: a fiber pattern removal algorithm and a spectrum correction for fiber bundles. The fiber pattern removal algorithm further includes three steps: determination of fiber core pixels location, Delaunay triangulation and Barycentric interpolation reconstruction. Fiber core location is determined using white reference images. The positions of the fiber core pixels remain constant on each channel of the sample image if no movement occurs at the camera-bronchoscope interface. Delaunay triangulation and Barycentric interpolation are applied to both the white reference images and sample images (16-channel hypercube). The techniques and systems described in the present disclosure can reconstruct missing space using one or more specified algorithms (e.g., RGB images and hyperspectral images) and correct distortions on hyperspectral snapshot cameras with super-Bayer filter approaches (e.g., hyperspectral). The method serves as an enhancement of the combination of imaging techniques providing a simplified, fast, robust and versatile fiber pattern removal method for snapshot hyperspectral images. The techniques and systems described in the present disclosure do not require any scanning opto-mechanics or special controllers. The process of endoscopic image acquisition is simplified and the initial instrumental cost is effectively decreased. In addition, the image processing method can be applied in semi-real time with high frame rate or as a post processing method. The algorithm versatility makes it applicable to a variety of snapshot mosaic hyperspectral cameras working with different fiber-bundle endoscopes. Flexibility of the endoscopic system enables access of hyperspectral imaging to inner hollow cavities of animals and human bodies with minimal invasiveness.

Figure 1:
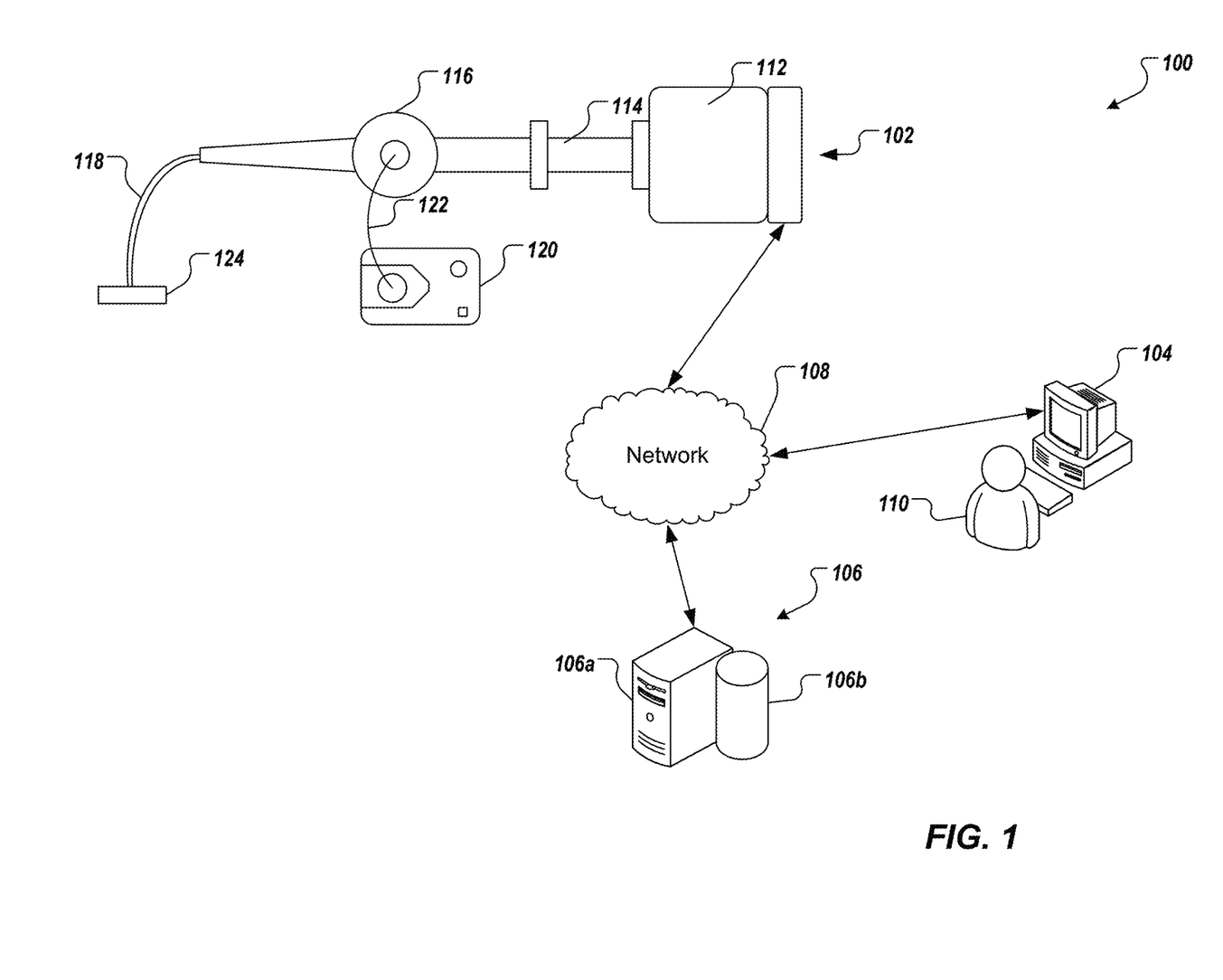
FIG. 1 depicts an example of an architecture that can be used to realize implementations of the present disclosure.

FIG. 1 depicts an example of an architecture 100 that can be used to realize implementations of the present disclosure. The architecture 100 includes an endoscopic system 102 and a computing device 104 communicably connected to a back-end system 106 by a network 108. In some implementations, the computing device 104 is directly connected to or integrated within the endoscopic system 102. The endoscopic system 102 and the computing device 104 can be operated by a user 110.

The endoscopic system 102 includes a mosaic hyperspectral camera 112, an adapter 114, a bronchoscope 116, a fiber bundle 118, a light source 120, and a light guide cable 122. The endoscopic system 102 can be configured to visualize a tissue sample 124. In one exemplary embodiment according to the present invention, a plurality of light sources, for example light generated by a halogen light source 120 is used. The light is sent by the bronchoscope 116 to a distal tip of a fiber bundle 118 via one or more optical fibers, formed into a beam, and the beam is scanned across a field-of-view (FOV). At least a portion of the light reflected, scattered, refracted, or otherwise perturbed by the FOV is gathered and converted into electrical signals that are acquired by the mosaic hyperspectral camera 112. The mosaic hyperspectral camera 112 can be a snapshot complementary metal-oxide semiconductor (CMOS) mosaic hyperspectral camera. The mosaic hyperspectral camera 112 can include a super-Bayer filter with 16 physical channels layout (e.g., SM4x4-460-630, IMEC, Leuven, Belgium). For example, the snapshot mosaic hyperspectral camera has 16 physical channels, which physically consists of 512x256 4x4 Bayer filters on the sensor. In some implementations, the peak wavelengths of these channels are not evenly distributed in the active wavelength range (VIS 470-630 nm) and one or more channels have the second order response. By combining information about beam position and the amount of light gathered, a digital image can be formed.

The adapter 114 can be configured to connect the mosaic hyperspectral camera 112 to the bronchoscope 116, enabling transmission in the visible spectrum. The adapter 114 can perform sealing and instrument-locking functions without requiring replacement of an attachment during the imaging procedure. The adapter 114 can include a 1:2.5 matched pair 400-700 nm, 35 mm bronchoscope adapter (Thorlabs, Newton, N.J., USA). In some implementations, the adapter 114 can include a long pass filter (OD4—475 nm/25 mm, Edmund, Barrington, N.J., USA) and a short pass filter (OD4—650 nm/25 mm, Edmund, Barrington, N.J., USA).

The bronchoscope 116 can be a commercial bronchoscope (e.g., PortaView® LF-TP, Olympus, Tokyo, Japan). The bronchoscope 116 can be configured to be inserted in the tracheal tube of a subject. For example, the outer diameter of the bronchoscope 116 can be less than 6 mm. The bronchoscope 116 is connected to the fiber bundle 118. The fiber bundle 118 is an elongate, generally tubular member that is sized to pass through an opening of a human patient or an animal (e.g., larynx, trachea and bronchi). The fiber bundle 118 can be configured to evenly illuminate surrounding tissues 124 for image acquisition. The fiber bundle 118 includes a shaft and a cap that secures the imaging system to the distal tip of the shaft. The shaft includes a major portion (e.g., including the proximal end region) with a central axis that defines a primary axis of the fiber bundle 118, the distal tip, and a distal bend that connects the major portion to the distal tip. The shaft defines a lumen that houses a plurality of optical fibers and one or more electrical cables of the imaging system. The shaft can be configured to allow for passage of fluids between the distal tip and the connection hub, and allows for passage of a working tool extending distally from connection hub. The shaft is typically made of one or more materials that are flexible enough to allow the fiber bundle 118 to bend by a small amount to be appropriately placed within the patient as desired, yet stiff enough to permit easy insertion into the respiratory canal. Examples of materials, from which the shaft is typically made include nylon, polysulfone, and polyether ether ketone (PEEK). The shaft is typically manufactured primarily via extrusion and via secondary processes that may include one or more of punching, laser cutting, forming, and/or printing. The cap is typically made of one or more materials including liquid crystal polymer (LCP) and is typically secured to the distal tip of the shaft via adhesive. The light source 120 can be configured to generate a light beam with a particular wavelength (e.g., 320 nm to 1100 nm). For example, the light source 120 can be a halogen light source (e.g., Olympus CLK-4). The light guide cable 122 can be configured to direct the light from the light source 120 to the bronchoscope 116. The light guide cable 122 can be a 4.25 mm, 3 m, CF type light guide (Olympus, Tokyo, Japan).

The computing device 104 includes a display for viewing images acquired by the endoscopic system 102 and processed by the computing device 104. In some examples, the computing device 104 can be a laptop computer, a desktop computer, a smartphone, a personal digital assistant, a portable media player, a tablet computer, or any other appropriate computing device that can be used to interface with the endoscopic system 102 and, in some implementations, communicate with the back-end system 106. In some examples, the back-end system 106 can include one or more computing devices 106a, such as a server, and one or more database systems 106b. In some examples, the back-end system 106 can represent more than one computing device working together to perform the actions of a server (e.g., cloud computing).

In some implementations, the database system 106b is provided as an in-memory database system. In some examples, an in-memory database is a database management system that uses main memory for data storage. In some examples, main memory includes random access memory (RAM) that communicates with one or more processors (e.g., central processing units (CPUs)) over a memory bus. An in-memory database can be contrasted with database management systems that employ a disk storage mechanism. In some examples, in-memory databases are faster than disk storage databases, because internal optimization algorithms can be simpler and execute fewer CPU instructions (e.g., require reduced CPU time consumption). In some examples, accessing data in an in-memory database eliminates seek time when querying the data, which provides faster and more predictable performance than disk-storage database systems.

In some examples, the network 108 can be a public communication network (e.g., the Internet, cellular data network, dialup modems over a telephone network), a wide area network (WAN), a local area network (LAN), e.g., an Ethernet cable, a private communications network (e.g., private LAN, leased lines), or any appropriate combination thereof.

In accordance with implementations of the present disclosure, the back-end system 106 can host one or more enterprise systems. In some examples, an enterprise system can be provided as one or more computer-executable programs executed by one or more computing devices. Examples of enterprise systems can include applications that support industry, military, security, and medical (e.g., endoscopy) fields.

In some implementations, an endoscopic system 102 can be provided in an image acquisition and processing mode, during which users interact with the endoscopic system to access and visualize a tissue portion across the electromagnetic spectrum or the visible spectrum. During operation in the image acquisition mode, data that is generated and acquired across the electromagnetic spectrum can be referred to as hyperspectral imaging data. During operation in the image acquisition mode, data that is generated and acquired across the visible spectrum can be referred to as RGB imaging data. In some implementations, a user 110 (e.g., an administrator of the enterprise system, a qualified medical personnel, a security engineer or a soldier) can use the computing device 104 to perform image processing operations, as described in further detail with reference to FIG. 2.

Figure 2:
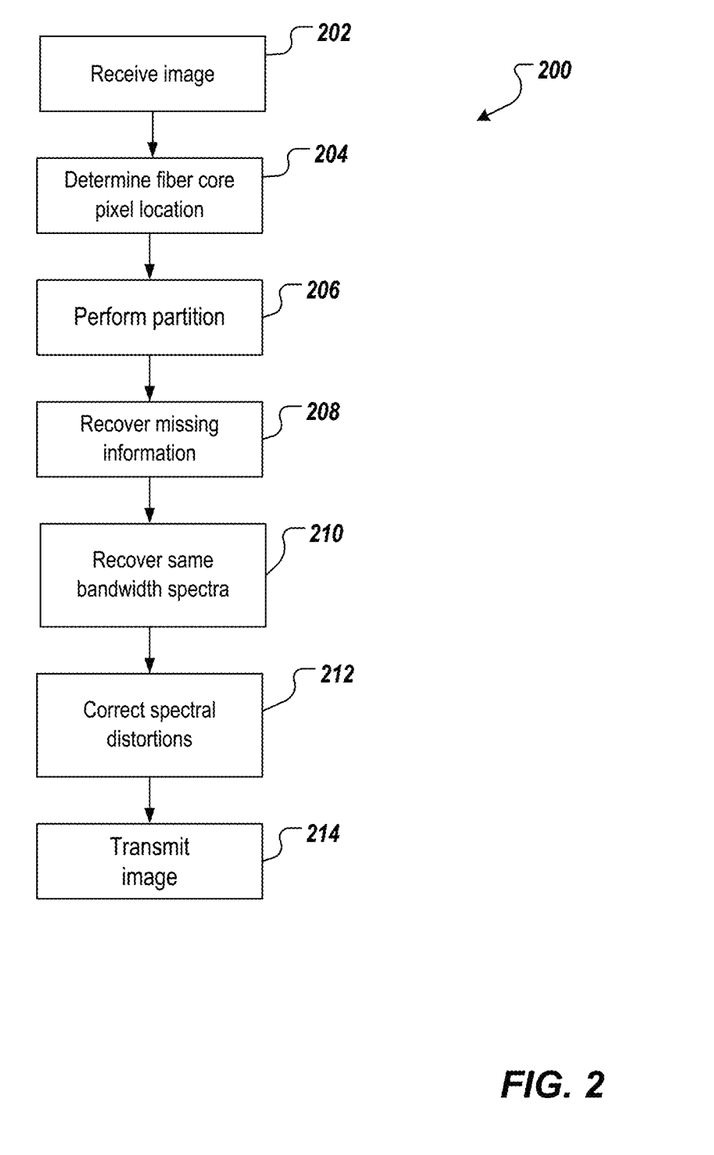
FIG. 2 depicts an example of a process that can be executed in accordance with implementations of the present disclosure.

FIG. 2 depicts an example of an image reconstruction process 200 that can be executed in accordance with implementations of the present disclosure. In some implementations, the process 200 can be realized using one or more computer-executable programs executed using one or more computing devices.

At 202, an image is received by a computing device (e.g., computing device 104 described with reference to FIG. 1) from an endoscopic system including an optical fiber bundle including multiple optical fibers (channels), each optical fiber being surrounded by cladding (e.g., endoscopic system 102 described with reference to FIG. 1). The received image can include a hyperspectral or a RGB image. In some implementations, the image is received in real time (e.g., within milliseconds after acquisition). From 202, method 200 proceeds to 204.

At 204, the fiber core pixel locations corresponding to the optical fibers included in the optical fiber bundle are determined for images received by the computing device. The fiber core pixels are localized using a reference image (e.g., a monochromatic white or grey image). The fiber core pixels with the highest intensity value among one fiber are identified as fiber core pixels and used as the interpolation source. The light coming out from the optical fiber is modeled using an interpolation function (e.g., a Gaussian function, or nearest neighbor interpolation) to reconstruct missing space (e.g., data that would be present in the acquired image but for the cladding on the fiber bundle) without introducing artifacts. Due to the known filter configuration (e.g., 4×4 Bayer filters), the fiber core pixel has relatively identical locations in each channel. The image precision can be improved by locating fiber core pixels for each optical fiber (e.g., 16 channels). In some implementations, the reference image can be used for spectrum calibration (FIGS. 3A-3E). Light source intensity conditions can be optimized to avoid saturation while filling a particular percentage (e.g., approximately 80% to approximately 85%) of a particular pixel depth (e.g., 10-bit pixel depth). The settings, acquired on a high percentage (e.g., approximately 99%) reflectance standard color target (e.g., SRS-99-010, Labsphere®, North Sutton, USA) can provide image acquisition with the samples. The uniformity of the reflectance target allows for localization of all fiber cores. The process can be challenging on a real sample where unevenness of intensity values might fall below the sensor's Gaussian noise. For example, the maximum noise value can be measured at a particular intensity (e.g., 70 in 10-bits).

The fiber core pixels localization method can be summarized in three parts. For example, a threshold $T_i$, i=1, 2 ... 16 is chosen for each channel to remove the cladding pixels. The value of $T_i$ can depend on the illumination settings. The first round of fiber core pixel candidates are selected for screening. The fiber pixel candidates of each channel are chosen using an algorithm that finds 2D local maxima. In the optical configuration, each fiber approximately illuminates an area with a particular size (e.g., a 3×3 pixel area). A mask with a size matching the illuminated area (e.g., a 3×3 pixel mask) is utilized to scan the multi-channel (e.g., 16-channel) images (e.g., border extended images) in raster order. If the center pixel of the mask is higher than a selected number (e.g., 8) of connected neighbor pixels, the center pixel is chosen as the fiber core pixel candidate $P_k$, k=1 . . . N.

The second round fiber core pixels screening is performed to remove incorrect core pixels (e.g., false positive coordinates) using relative distance analysis to generate a reconstructed image. The N fiber core pixel candidates $P_k$, k=1 N, are sorted in descending order based on intensity values. A mask is defined with size L×L, where L depends on the distance of nearby fiber core pixels. In this case, the horizontal and vertical distance is a particular number n of pixels (e.g., 4 pixels), a target value for L can be smaller than the vertical distance (e.g., 3 pixels). Following the sorting order, the current candidate is used as the center of the mask and it is verified whether any of the selected number (e.g., 8) of connected neighbor pixel was previously identified as a candidate. If other candidate pixels are present, the candidate with lower intensity is discarded. Flood fill algorithm can be used for implementing the second round of screening. In some implementations, the mask-based approach can be used for implementing the second round of screening, which reduces computation costs and provides time efficiency. From 204, method 200 proceeds to 206.

At 206, the image is partitioned into regions based on a selected distance to points in a particular subset (e.g., using Voronoi diagrams). Fiber core pixel positions for each channel serve as an input for generating a partitioning diagram. In some implementations, fiber core pixel positions for each channel serve as an input for generating a Voronoi diagram using Delaunay triangulation method. As a result, every pixel of each channel is enclosed in one triangle with vertices corresponding to the closest three fiber core centers. Representative partitioning (e.g., Delaunay triangulation) results can be generated for the region of interest (ROI) of each channel within the white reference image (FIG. 3B) and the sample image (FIG. 3H). From 206, method 200 proceeds to 208.

At 208, missing information is recovered to generate fiber-pattern removed images. In some implementations, the fiber pattern is removed using an interpolation method (e.g., Barycentric interpolation method). In some implementations, the selected interpolation method is a linear interpolation method based on a particular number (e.g., three) of source points (e.g., $v_1$, $v_2$ and $v_3$). In some implementations, the source points correspond to the fiber core centers. The areas defined by the source points (e.g., $A_1$, $A_2$ and $A_3$) can serve as interpolation (e.g., Barycentric) coordinates. The intensity value I(p) of any pixel p located inside each area (e.g., Delaunay triangle) can be estimated with the selected number (e.g., three) of fiber core pixels using the interpolation (e.g., Barycentric interpolation).

$$I(p) = \frac{A_1}{A_1+A_2+A_3} \cdot I(v_1) + \frac{A_2}{A_1+A_2+A_3} \cdot I(v_2) + \frac{A_3}{A_1+A_2+A_3} \cdot I(v_3) \quad (1)$$

From 208, method 200 proceeds to 210.

At 210, the same-bandwidth spectra are recovered from the snapshot mosaic (hyperspectral) camera sensor to process the images with removed fiber pattern. The snapshot mosaic (hyperspectral) camera has multiple (e.g., 16) physical channels. Several channels have a second order response. Crosstalk can exist between the channels. In some implementations, the sensor manufacturer can provide a correction matrix transforming the images corresponding to the total number of channels (e.g., 16 channels images) to another N virtual channels (e.g., for the camera N=13), which can be used to recover the sample spectrum. The original number of channels (e.g., 16 channels) can be linearly transformed to a smaller number of channels (e.g., 13 channels) with same spatial size (e.g., 512×256) for each channel as follows:

$$R_{original} = \frac{E_{whiteref}}{E_{sample}} \frac{I_{sample} - I_{darkref_{sample}}}{I_{whiteref} - I_{darkref_{whiteref}}} \quad (2)$$

$$R_{corrected} = R_{original} \times T \quad (3)$$

The notation $R_{original}$ corresponds to a 2D reflectance matrix with the spatial size multiplied by the number of original channels, such as (512×256)×16. $E_{whiteref}$ and $E_{sample}$ are respectively the exposure time of white reference image and sample image. $I_{sample}$, $I_{whiteref}$, $I_{darkref_{sample}}$ and $I_{darkref_{whiteref}}$ are respectively the reshaped 2D hypercube of sample with original number of channels (e.g., 16-channels), white reference and two dark references. $I_{darkref_{sample}}$ and $I_{darkref_{whiteref}}$ are acquired by using the same exposure time respectively of sample image and white reference image and with the sensor being black out. T is a correction matrix with dimensions corresponding to the original number of channels and number of virtual channels (e.g., 16×13). $R_{corrected}$ is the spectrum corrected reflectance matrix that was linearly transformed and has a spatial size multiplied by the number of virtual channels (e.g., (512×256)×13). The 2D reflectance matrix is reshaped to generate a 3D reflectance matrix (e.g., with the size 512×256×13). The method of generating the same-bandwidth spectra can vary depending on the (hyperspectral) camera in use (e.g., the number of channels and matrices can vary). After 210, method 200 proceeds to 212.

At 212, correction of spectral distortions (e.g., artifacts) of generated same-bandwidth spectra images is performed to generate corrected images. Intensities of light with different wavelengths are likely to be distorted differently during the transmission through a fiber based on the fiber configuration, resulting in a distorted recovered spectrum. A mathematical method is used to minimize the spectral distortion. In some implementations, a particular imaging configuration is used to acquire the images of six standard color targets (red: SCS-RD-010, green: SCS-GN-010, blue: SCS-BL-010, yellow: SCS-YW-010, grey 20% reflectance: SRS-20-010, grey 50% reflectance: SRS-50-010, Labsphere®, North Sutton, USA) under the same light condition. The fiber pattern is removed from each of the selected number (e.g., six) images. A reshaped reflectance matrix $R_{corrected}$ (e.g., with size 512×256×13) is generated for each of the color targets (e.g., six images). The average reflectance spectra is determined within each color target obtaining a matrix of reflectance spectra $r_{ij}$ in which i ranges from 1 to the number of virtual channels (e.g., i=1, 2, . . . , 13) representing the index of virtual channel, and j is the index of color target (e.g., j=1, 2, . . . 6). The color target manufacturer provides the calibrated reference reflectance spectra, called $s_{ij}$. For each of the virtual channels, a weight factor $w_i$ is used to minimize the mean square error ($MSE_i$ provided by equation 4) with respect to the reference target. Because the second order derivative of $MSE_i$ is a positive real number, $MSE_i$ is a convex function of $w_i$. $MSE_i$ is derived with respect to $w_i$ and it is set to be zero, obtaining the optimized solution (equation 5) for each channel.

$$MSE_i = (\underline{s_i} - w_i \underline{r_i})^T (\underline{s_i} - w_i \underline{r_i}), \, i = 1, 2 \ldots 13 \quad (4)$$

$$w_i = \frac{\underline{s_i}^T \underline{r_i}}{\underline{r_i}^T \underline{r_i}}, \, i = 1, 2 \ldots 13 \quad (5)$$

The resulting weight factor w is used as a correction matrix is applied to the corrected reflectance matrix (equation 6) to generate the final reflectance matrix $R_{final}$.

$$R_{final,i} = w_i \cdot R_{correct,i} \quad (6)$$

After 212, method 200 proceeds to 214. At 214, the images corresponding to the final reflectance matrix can be transmitted over a network to a database for storage. In some implementations, the process 200 is performed in semi-real time (e.g., within milliseconds-seconds from image acquisition) with high frame rate such that, method 200 loops back to 204. For example, a series of images can be acquired, processed and combined ("stitched") to obtain a larger field of view (e.g., three-dimensional view) with a higher dynamic range and better resolution. In some implementations, the stitching of the images can be performed using XuvTools®, provided by Oxford Instruments.

Figures 3A, 3J:
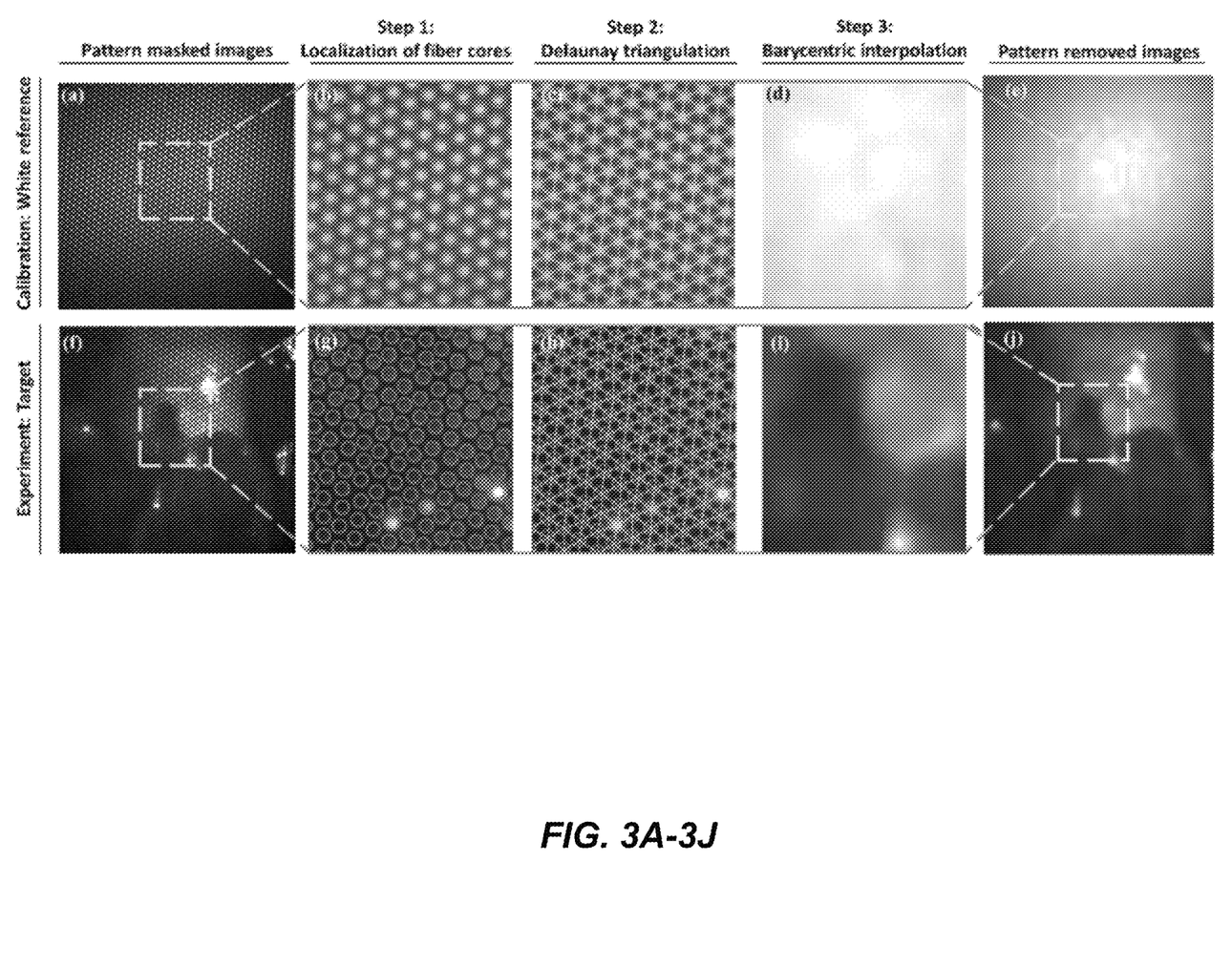

FIGS. 3A-3J illustrate a fiber pattern removal algorithm diagram for a white reference image (FIGS. 3A-3E) and an experimental target image (FIGS. 3F-3J). FIG. 3A illustrates a pattern masked white reference image. FIG. 3B illustrates localization of fiber cores in the pattern masked white reference image. FIG. 3C illustrates Delaunay triangulation in the white reference image with localized fiber cores. FIG. 3D illustrates Barycentric interpolation in the white reference image with Delaunay triangulation. FIG. 3E illustrates the white reference image with the pattern removed.

FIG. 3F illustrates a pattern masked experimental target image. FIG. 3G illustrates localization of fiber cores in the pattern masked experimental target image. FIG. 3H illustrates Delaunay triangulation in the experimental target image with localized fiber cores. FIG. 3I illustrates Barycentric interpolation in the experimental target image with Delaunay triangulation. FIG. 3J illustrates the experimental target image with the pattern removed. The results of spectral calibration for fiber bundles indicate the improvement of the image quality after associated to the fiber pattern removal algorithm.

Figure 4A:
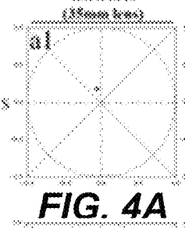
FIGS. 4A-4R illustrate an example of a hyperspectral phasor analysis on color targets and color checkers in accordance with implementations of the present disclosure.
Figure 4B:
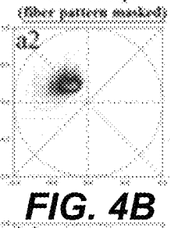
Figure 4C:
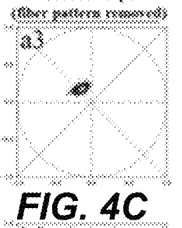
Figure 4D:
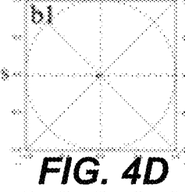
Figure 4E:
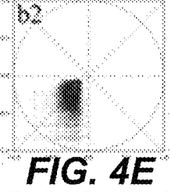
Figure 4F:
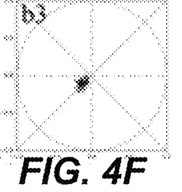
Figure 4G:
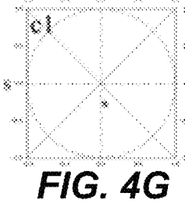
Figure 4H:
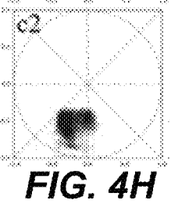
Figure 4I:
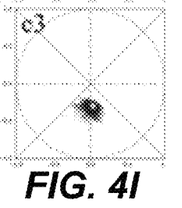
Figure 4J:
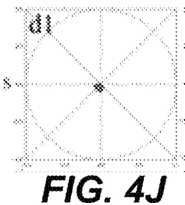
Figure 4K:
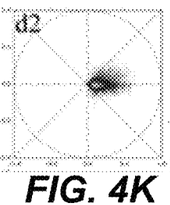
Figure 4L:
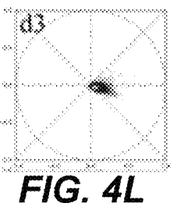
Figure 4M:
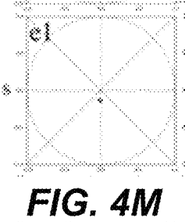
Figure 4N:
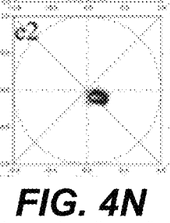
Figure 4O:
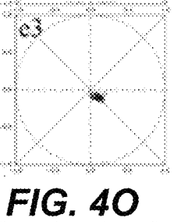
Figure 4P:
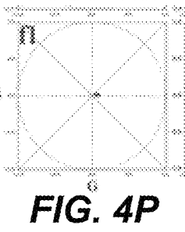
Figure 4Q:
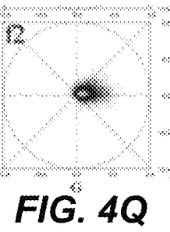
Figure 4R:
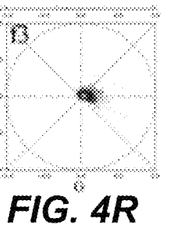

FIGS. 4A-4R illustrate hyperspectral phasor analysis on color targets and color checkers in accordance with implementations of the present disclosure. FIG. 4A illustrates a phasor plot of reference images acquired with a 35 mm lens for blue color target (e.g., SCS-BL-010, Labsphere). FIG. 4B illustrates a phasor plot of fiber pattern masked images for blue color target. FIG. 4C illustrates a phasor plot of fiber pattern removed images for blue color target.

FIG. 4D illustrates a phasor plot of reference images acquired with a 35 mm lens for green color target (e.g., SCS-GN-010, Labsphere). FIG. 4E illustrates a phasor plot of fiber pattern masked images for green color target. FIG. 4F illustrates a phasor plot of fiber pattern removed images for green color target.

FIG. 4G illustrates a phasor plot of reference images acquired with a 35 mm lens for red color target (e.g., SCS-RD-010, Labsphere). FIG. 4H illustrates a phasor plot of fiber pattern masked images for red color target. FIG. 4I illustrates a phasor plot of fiber pattern removed images for red color target.

FIG. 4J illustrates a phasor plot of reference images acquired with a 35 mm lens for brown color target (e.g., ColorChecker Classic Card, X-Rite). FIG. 4K illustrates a phasor plot of fiber pattern masked images for brown color target. FIG. 4L illustrates a phasor plot of fiber pattern removed images for brown color target.

FIG. 4M illustrates a phasor plot of reference images acquired with a 35 mm lens for yellow color target (e.g., ColorChecker Classic Card, X-Rite). FIG. 4N illustrates a phasor plot of fiber pattern masked images for yellow color target. FIG. 4O illustrates a phasor plot of fiber pattern removed images for yellow color target.

FIG. 4P illustrates a phasor plot of reference images acquired with a 35 mm lens for neutral color target (e.g., 3.5 (grey) color checker, ColorChecker Classic Card, X-Rite). FIG. 4Q illustrates a phasor plot of fiber pattern masked images for neutral color target. FIG. 4R illustrates a phasor plot of fiber pattern removed images for neutral color target.

FIGS. 4A-4R illustrate the improvement of fiber pattern removal, tested through a comparison between the spectra recovered from three images of color targets (red: SCS-RD-010, green: SCS-GN-010, blue: SCS-BL-010) and from three pattern masked images of color checkers (e.g., X-Rite ColorChecker® Classic, Grand Rapids, Mich., USA). The calibration was applied to both target images before and after fiber pattern removal algorithm. The reference spectra can be recovered from images acquired using a 35 mm Edmunds objective lens instead of a bronchoscope in particular light situations.

The fiber pattern in original endoscopic images can introduce undesired spectra into the hyperspectral matrix (FIGS. 4B, 4E, 4H, 4K, 4N, 4Q). The effect is represented by the spreading of the phasor plot. After applying fiber pattern removal algorithm to the images, the majority of undesired mixed spectra can be effectively suppressed (FIGS. 4C, 4F, 4I, 4L, 4O, 4R), reducing the spreading on the plot.

Two measurements of errors can be used: scatter error and shifted-mean error on the phasor plot, to quantify and compare the spectrum recovering performance. The scatter error represents how widely the spectrum spreads from the mean spectrum (mean phasor coordinates) due to instrumental and Poissonian noise on the multiple channels. Shifted-mean error represents the displacement of the mean spectrum of the observed sample image, in this case the ROI, from the mean of spectrum of reference image, here the 35 mm lens. The two error measures for reference images, fiber pattern masked images, and fiber pattern removed images illustrated in FIGS. 4A-4R are reported in Table 1.

TABLE 1

Scatter error and shifted-mean error

| Sample | Sample type | Scatter error | Shifted-mean error |
|---|---|---|---|
| Blue target | Reference | 0.017 | 0 |
| | Pattern masked | 0.132 | 0.217 |
| | Pattern removed | 0.052 | 0.091 |
| Green target | Reference | 0.013 | 0 |
| | Pattern masked | 0.412 | 0.392 |
| | Pattern removed | 0.036 | 0.072 |
| Red target | Reference | 0.023 | 0 |
| | Pattern masked | 0.183 | 0.375 |
| | Pattern removed | 0.121 | 0.089 |

TABLE 1-continued

Scatter error and shifted-mean error

| Sample | Sample type | Scatter error | Shifted-mean error |
|---|---|---|---|
| Brown color checker | Reference | 0.030 | 0 |
| | Pattern masked | 0.148 | 0.127 |
| | Pattern removed | 0.076 | 0.010 |
| Yellow color checker | Reference | 0.016 | 0 |
| | Pattern masked | 0.035 | 0.075 |
| | Pattern removed | 0.018 | 0.057 |
| Neutral3.5 color checker | Reference | 0.025 | 0 |
| | Pattern masked | 0.169 | 0.071 |
| | Pattern removed | 0.044 | 0.055 |

Scatter errors on fiber pattern removed images of color target and checkers are consistently smaller than those on pattern-masked images. The result highlights quantitatively the capability of the fiber pattern removal algorithm to suppress undesired spectra. The fiber pattern removal algorithm improves the recovery of the original spectra as indicated by the reduced shifted mean error.

Figure 5:
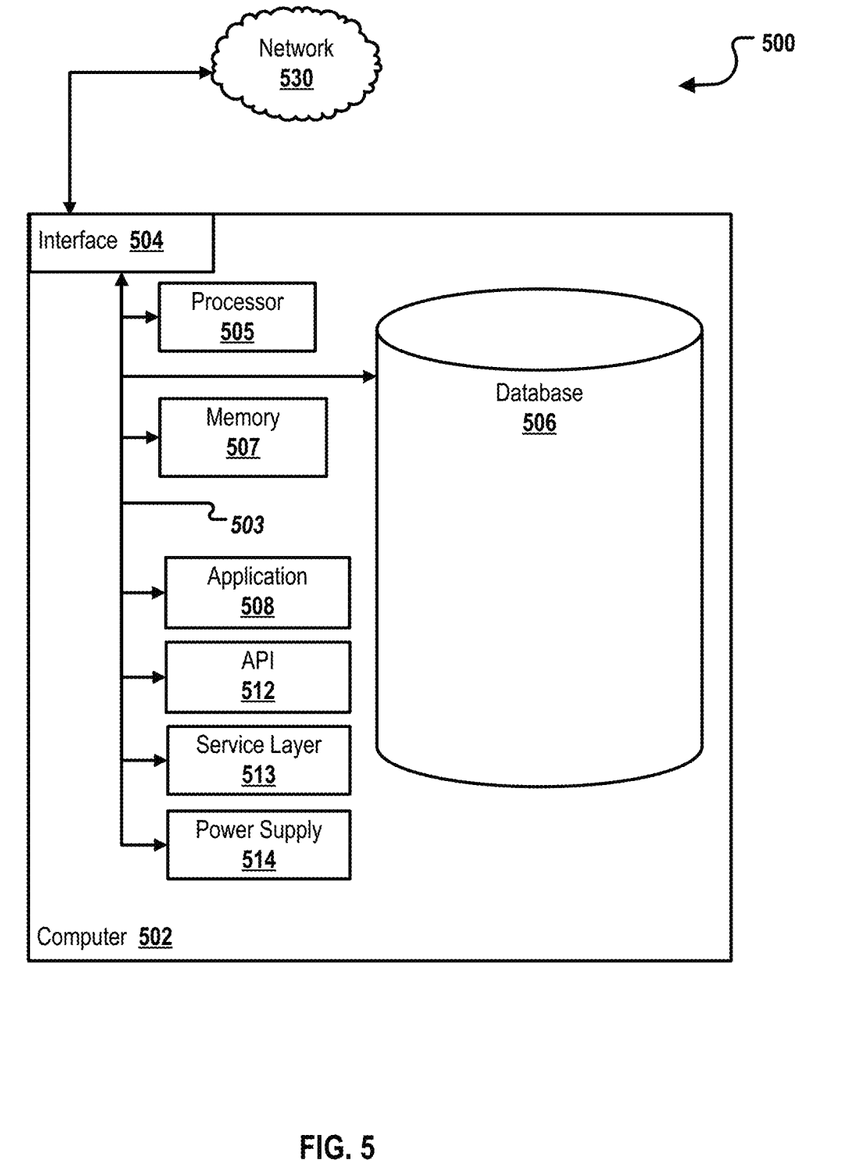
FIG. 5 is a block diagram illustrating an example of a computer-implemented system used to provide computational functionalities associated with described algorithms, methods, functions, processes, flows, and procedures, according to an implementation of the present disclosure.

FIG. 5 is a block diagram illustrating an example of a computer-implemented System 500 used to provide computational functionalities associated with described algorithms, methods, functions, processes, flows, and procedures, according to an implementation of the present disclosure. In the illustrated implementation, System 500 includes a Computer 502 and a Network 530.

The illustrated Computer 502 is intended to encompass any computing device such as a server, desktop computer, laptop/notebook computer, wireless data port, smart phone, personal data assistant (PDA), tablet computer, one or more processors within these devices, another computing device, or a combination of computing devices, including physical or virtual instances of the computing device, or a combination of physical or virtual instances of the computing device. Additionally, the Computer 502 can include an input device, such as a keypad, keyboard, touch screen, another input device, or a combination of input devices that can accept user information, and an output device that conveys information associated with the operation of the Computer 502, including digital data, visual, audio, another type of information, or a combination of types of information, on a graphical-type user interface (UI) (or GUI) or other UI.

The Computer 502 can serve in a role in a distributed computing system as a client, network component, a server, a database or another persistency, another role, or a combination of roles for performing image reconstruction as described in the present disclosure. The illustrated Computer 502 is communicably coupled with a Network 530. In some implementations, one or more components of the Computer 502 can be configured to operate within an environment, including cloud computing based, local, global, another environment, or a combination of environments.

At a high level, the Computer 502 is an electronic computing device operable to receive, transmit, process, store, or manage data and information associated with the described subject matter. According to some implementations, the Computer 502 can also include or be communicably coupled with a server, including an application server, email server, web server, caching server, streaming data server, another server, or a combination of servers.

The Computer 502 can receive requests over Network 530 (for example, from a client software application executing on another Computer 502) and respond to the received requests by processing the received requests using a software application or a combination of software applications. In addition, requests can also be sent to the Computer 502 from internal users (for example, from a command console or by another internal access method), external or third parties, or other entities, individuals, systems, or computers.

Each of the components of the Computer 502 can communicate using a System Bus 503. In some implementations, any or all of the components of the Computer 502, including hardware, software, or a combination of hardware and software, can interface over the System Bus 503 using an application-programming interface (API) 512, a Service Layer 513, or a combination of the API 512 and Service Layer 513. The API 512 can include specifications for routines, data structures, and object classes. The API 512 can be either computer-language independent or dependent and refer to a complete interface, a single function, or even a set of APIs. The Service Layer 513 provides software services to the Computer 502 or other components (whether illustrated or not) that are communicably coupled to the Computer 502. The functionality of the Computer 502 can be accessible for all service consumers using the Service Layer 513. Software services, such as those provided by the Service Layer 513, provide reusable, defined functionalities through a defined interface. For example, the interface can be software written in JAVA, C++, another computing language, or a combination of computing languages providing data in extensible markup language (XML) format, another format, or a combination of formats. While illustrated as an integrated component of the Computer 502, some implementations can illustrate the API 512 or the Service Layer 513 as stand-alone components in relation to other components of the Computer 502 or other components (whether illustrated or not) that are communicably coupled to the Computer 502. Moreover, any or all parts of the API 512 or the Service Layer 513 can be implemented as a child or a sub-module of another software module, enterprise application, or hardware module without departing from the scope of the present disclosure.

The Computer 502 includes an Interface 504. Although illustrated as a single Interface 504, two or more Interfaces 504 can be used according to particular needs, desires, or particular implementations of the Computer 502. The Interface 504 is used by the Computer 502 for communicating with another computing system (whether illustrated or not) that is communicatively linked to the Network 530 in a distributed environment. Generally, the Interface 504 is operable to communicate with the Network 530 and includes logic encoded in software, hardware, or a combination of software and hardware. More specifically, the Interface 504 can include software supporting one or more communication protocols associated with communications such that the Network 530 or hardware of Interface 504 is operable to communicate physical signals within and outside of the illustrated Computer 502.

The Computer 502 includes a Processor 505. Although illustrated as a single Processor 505, two or more Processors 505 can be used according to particular needs, desires, or particular implementations of the Computer 502. Generally, the Processor 505 executes instructions and manipulates data to perform the operations of the Computer 502 and any algorithms, methods, functions, processes, flows, and procedures as described in the present disclosure.

The Computer 502 also includes a Database 506 that can hold data for the Computer 502, another component communicatively linked to the Network 530 (whether illustrated or not), or a combination of the Computer 502 and another component. For example, Database 506 can be an in-memory, disk storage, or another type of database storing data consistent with the present disclosure. In some implementations, Database 506 can be a combination of two or more different database types (for example, a hybrid in-memory and disk storage database) according to particular needs, desires, or particular implementations of the Computer 502 and the described functionality. Although illustrated as a single Database 506, two or more databases of similar or differing types can be used according to particular needs, desires, or particular implementations of the Computer 502 and the described functionality. While Database 506 is illustrated as an integral component of the Computer 502, in some implementations, Database 506 can be external to the Computer 502.

The Computer 502 also includes a Memory 507 that can hold data for the Computer 502, another component or components communicatively linked to the Network 530 (whether illustrated or not), or a combination of the Computer 502 and another component. Memory 507 can store any data consistent with the present disclosure. In some implementations, Memory 507 can be a combination of two or more different types of memory (for example, a combination of semiconductor and magnetic storage) according to particular needs, desires, or particular implementations of the Computer 502 and the described functionality. Although illustrated as a single Memory 507, two or more Memories 507 of similar or differing types can be used according to particular needs, desires, or particular implementations of the Computer 502 and the described functionality. While Memory 507 is illustrated as an integral component of the Computer 502, in some implementations, Memory 507 can be external to the Computer 502.

The Application 508 is an algorithmic software engine providing functionality according to particular needs, desires, or particular implementations of the Computer 502, particularly with respect to functionality described in the present disclosure. For example, Application 508 can serve as one or more components, modules, or applications. Further, although illustrated as a single Application 508, the Application 508 can be implemented as multiple Applications 508 on the Computer 502. In addition, although illustrated as integral to the Computer 502, in some implementations, the Application 508 can be external to the Computer 502.

The Computer 502 can also include a Power Supply 514. The Power Supply 514 can include a rechargeable or non-rechargeable battery that can be configured to be either user- or non-user-replaceable. In some implementations, the Power Supply 514 can include power-conversion or management circuits (including recharging, standby, or another power management functionality). In some implementations, the Power Supply 514 can include a power plug to allow the Computer 502 to be plugged into a wall socket or another power source to, for example, power the Computer 502 or recharge a rechargeable battery.

There can be any number of Computers 502 associated with, or external to, a computer system containing Computer 502, each Computer 502 communicating over Network 530. Further, the term "client," "user," or other appropriate terminology can be used interchangeably, as appropriate, without departing from the scope of the present disclosure. Moreover, the present disclosure contemplates that many users can use one Computer 502, or that one user can use multiple Computers 502.

Described implementations of the subject matter can include one or more features, alone or in combination.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs, that is, one or more modules of computer program instructions encoded on a tangible, non-transitory, computer-readable medium for execution by, or to control the operation of, a computer or computer-implemented system. Alternatively, or additionally, the program instructions can be encoded in/on an artificially generated propagated signal, for example, a machine-generated electrical, optical, or electromagnetic signal that is generated to encode information for transmission to a receiver apparatus for execution by a computer or computer-implemented system. The computer-storage medium can be a machine-readable storage device, a machine-readable storage substrate, a random or serial access memory device, or a combination of computer-storage mediums. Configuring one or more computers means that the one or more computers have installed hardware, firmware, or software (or combinations of hardware, firmware, and software) so that when the software is executed by the one or more computers, particular computing operations are performed.

The term "semi-real-time," "real time," "realtime," "real (fast) time (RFT)," "near(ly) real-time (NRT)," "quasi real-time," or similar terms (as understood by one of ordinary skill in the art), means that an action and a response are temporally proximate such that an individual perceives the action and the response occurring substantially simultaneously. For example, the time difference for a response to display (or for an initiation of a display) of data following the individual's action to access the data can be less than 1 millisecond (ms), less than 1 second (s), or less than 5 s. While the requested data need not be displayed (or initiated for display) instantaneously, it is displayed (or initiated for display) without any intentional delay, taking into account processing limitations of a described computing system and time required to, for example, gather, accurately measure, analyze, process, store, or transmit the data.

The terms "data processing apparatus," "computer," or "electronic computer device" (or an equivalent term as understood by one of ordinary skill in the art) refer to data processing hardware. Data processing hardware encompass all kinds of apparatuses, devices, and machines for processing data, including by way of example, a programmable processor, a computer, or multiple processors or computers. The computer can also be, or further include special purpose logic circuitry, for example, a central processing unit (CPU), a field programmable gate array (FPGA), or an application-specific integrated circuit (ASIC). In some implementations, the computer or computer-implemented system or special purpose logic circuitry (or a combination of the computer or computer-implemented system and special purpose logic circuitry) can be hardware- or software-based (or a combination of both hardware- and software-based). The computer can optionally include code that creates an execution environment for computer programs, for example, code that constitutes processor firmware, a protocol stack, a database management system, an operating system, or a combination of execution environments. The present disclosure contemplates the use of a computer or computer-implemented system with an operating system of some type, for example LINUX, UNIX, WINDOWS, MAC OS, ANDROID, IOS, another operating system, or a combination of operating systems.

A computer program, which can also be referred to or described as a program, software, a software application, a unit, a module, a software module, a script, code, or other component can be written in any form of programming language, including compiled or interpreted languages, or declarative or procedural languages, and it can be deployed in any form, including, for example, as a stand-alone program, module, component, or subroutine, for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network.

While portions of the programs illustrated in the various figures can be illustrated as individual components, such as units or modules, that implement described features and functionality using various objects, methods, or other processes, the programs can instead include a number of sub-units, sub-modules, third-party services, components, libraries, and other components, as appropriate. Conversely, the features and functionality of various components can be combined into single components, as appropriate. Thresholds used to make computational determinations can be statically, dynamically, or both statically and dynamically determined.

Described methods, processes, or logic flows represent one or more examples of functionality consistent with the present disclosure and are not intended to limit the disclosure to the described or illustrated implementations, but to be accorded the widest scope consistent with described principles and features. The described methods, processes, or logic flows can be performed by one or more programmable computers executing one or more computer programs to perform functions by operating on input data and generating output data. The methods, processes, or logic flows can also be performed by, and computers can also be implemented as, special purpose logic circuitry, for example, a CPU, an FPGA, or an ASIC.

Computers for the execution of a computer program can be based on general or special purpose microprocessors, both, or another type of CPU. Generally, a CPU will receive instructions and data from and write to a memory. The essential elements of a computer are a CPU, for performing or executing instructions, and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable memory storage device.

Non-transitory computer-readable media for storing computer program instructions and data can include all forms of permanent/non-permanent or volatile/non-volatile memory, media and memory devices, including by way of example semiconductor memory devices, for example, random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices; magnetic devices, for example, tape, cartridges, cassettes, internal/removable disks; magneto-optical disks; and optical memory devices, for example, digital versatile/video disc (DVD), compact disc (CD)-ROM, DVD+/-R, DVD-RAM, DVD-ROM, high-definition/density (HD)-DVD, and BLU-RAY/BLU-RAY DISC (BD), and other optical memory technologies. The memory can store various objects or data, including caches, classes, frameworks, applications, modules, backup data, jobs, web pages, web page templates, data structures, database tables, repositories storing dynamic information, or other appropriate information including any parameters, variables, algorithms, instructions, rules, constraints, or references. Additionally, the memory can include other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a cathode ray tube (CRT), liquid crystal display (LCD), light emitting diode (LED), or plasma monitor, for displaying information to the user and a keyboard and a pointing device, for example, a mouse, trackball, or trackpad by which the user can provide input to the computer. Input can also be provided to the computer using a touchscreen, such as a tablet computer surface with pressure sensitivity, a multi-touch screen using capacitive or electric sensing, or another type of touchscreen. Other types of devices can be used to interact with the user. For example, feedback provided to the user can be any form of sensory feedback (such as, visual, auditory, tactile, or a combination of feedback types). Input from the user can be received in any form, including acoustic, speech, or tactile input. In addition, a computer can interact with the user by sending documents to and receiving documents from a client-computing device that is used by the user (for example, by sending web pages to a web browser on a user's mobile computing device in response to requests received from the web browser).

The term "graphical user interface," or "GUI," can be used in the singular or the plural to describe one or more graphical user interfaces and each of the displays of a particular graphical user interface. Therefore, a GUI can represent any graphical user interface, including but not limited to, a web browser, a touch screen, or a command line interface (CLI) that processes information and efficiently presents the information results to the user. In general, a GUI can include a number of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication (or a combination of data communication), for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20 (or a combination of 802.11x and 802.20 or other protocols consistent with the present disclosure), all or a portion of the Internet, another communication network, or a combination of communication networks. The communication network can communicate with, for example, Internet Protocol (IP) packets, frame relay frames, Asynchronous Transfer Mode (ATM) cells, voice, video, data, or other information between network nodes.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any inventive concept or on the scope of what can be claimed, but rather as descriptions of features that can be specific to particular implementations of particular inventive concepts. Certain features that are described in this specification in the context of separate implementations can also be implemented, in combination, in a single implementation. Conversely, various features that are described in the context of a single implementation can also be implemented in multiple implementations, separately, or in any sub-combination. Moreover, although previously described features can be described as acting in certain combinations and even initially claimed as such, one or more features from a claimed combination can, in some cases, be excised from the combination, and the claimed combination can be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations can be considered optional), to achieve desirable results. In certain circumstances, multitasking or parallel processing (or a combination of multitasking and parallel processing) can be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

What is claimed is:

1. A computer-implemented method for image reconstruction, the method being executed using one or more processors and comprising:
   receiving, by the one or more processors, an image acquired by an endoscopic system comprising an optical fiber bundle comprising a plurality of optical fibers, wherein each of the plurality of optical fibers is surrounded by cladding;
   determining, by the one or more processors, in the image a plurality of fiber core locations corresponding to the plurality of optical fibers in the optical fiber bundle;
   reconstructing, by the one or more processors, missing information from the image using interpolation performed in accordance with the plurality of fiber core locations, wherein the missing information corresponds to artifacts in the acquired image that result from the cladding;
   providing, by the one or more processors, a fiber-pattern removed image in which the artifacts in the acquired image are removed using the missing information; and
   performing, by the one or more processors, spectral correction for the fiber-pattern removed image by correcting spectral distortions associated with the endoscopic system.

2. The method of claim 1, wherein reconstructing the missing information comprises:
   performing, by the one or more processors, Delaunay triangulation on the plurality of fiber core locations to generate triangulation data; and
   performing, by the one or more processors, Barycentric interpolation using the triangulation data to produce the missing information.

3. The method of claim 2, wherein determining the plurality of fiber core locations in the image comprises localizing fiber core pixels using a reference image and a two dimensional Gaussian function to model light coming out from each of the plurality of optical fibers.

4. The method of claim 2, wherein determining the plurality of fiber core locations in the image comprises:
   performing, by the one or more processors, a first round of fiber core pixel candidate screening using individual threshold values set in accordance with illumination settings of the endoscopic system; and
   performing, by the one or more processors, a second round of fiber core pixel candidate screening to remove incorrect core pixels.

5. The method of claim 4, wherein performing the second round of fiber core pixel candidate screening comprises using a mask-based approach to remove incorrect core pixels.

6. The method of claim 1, wherein the image comprises a hyperspectral image.

7. The method of claim 6, wherein performing the spectral correction comprises:
recovering same-bandwidth spectra.

8. The method of claim 6, wherein performing the spectral correction comprises using a reshaped reflectance matrix.

9. The method of claim 1, wherein the receiving, the determining, the reconstructing, and the providing are performed in semi-real time.

10. A non-transitory computer-readable storage medium coupled to one or more processors and having instructions stored thereon which, when executed by the one or more processors, cause the one or more processors to perform operations for image reconstruction, the operations comprising:
receiving an image acquired by an endoscopic system comprising an optical fiber bundle comprising a plurality of optical fibers, wherein each of the plurality of optical fibers is surrounded by cladding;
determining in the image a plurality of fiber core locations corresponding to the plurality of optical fibers in the optical fiber bundle;
reconstructing missing information from the image using interpolation performed in accordance with the plurality of fiber core locations, wherein the missing information corresponds to artifacts in the acquired image that result from the cladding;
providing a fiber-pattern removed image in which the artifacts in the acquired image are removed using the missing information; and
performing spectral correction for the fiber-pattern removed image by correcting spectral distortions associated with the endoscopic system.

11. The computer-readable storage medium of claim 10, wherein reconstructing the missing information comprises:
performing Delaunay triangulation on the plurality of fiber core locations to generate triangulation data; and
performing Barycentric interpolation using the triangulation data to produce the missing information.

12. The computer-readable storage medium of claim 11, wherein determining the plurality of fiber core locations in the image comprises localizing fiber core pixels using a reference image and a two dimensional Gaussian function to model light coming out from each of the plurality of optical fibers.

13. The computer-readable storage medium of claim 11, wherein determining the plurality of fiber core locations in the image comprises:
performing a first round of fiber core pixel candidate screening using individual threshold values set in accordance with illumination settings of the endoscopic system; and
performing a second round of fiber core pixel candidate screening to remove incorrect core pixels.

14. The computer-readable storage medium of claim 13, wherein performing the second round of fiber core pixel candidate screening comprises using a mask-based approach to remove incorrect core pixels.

15. The computer-readable storage medium of claim 10, wherein the image comprises a hyperspectral image.

16. A system, comprising:
an endoscopic system;
a client-side computing device; and
a computer-readable storage device coupled to the client-side computing device and having instructions stored thereon which are configured to cause the client-side computing device to perform operations for image reconstruction, the operations comprising:
receiving an image acquired by an endoscopic system comprising an optical fiber bundle comprising a plurality of optical fibers, wherein each of the plurality of optical fibers is surrounded by cladding,
determining in the image a plurality of fiber core locations corresponding to the plurality of optical fibers in the optical fiber bundle,
reconstructing missing information from the image using interpolation performed in accordance with the plurality of fiber core locations, wherein the missing information corresponds to artifacts in the acquired image that result from the cladding,
providing a fiber-pattern removed image in which the artifacts in the acquired image are removed using the missing information, and
performing spectral correction for the fiber-pattern removed image by correcting spectral distortions associated with the endoscopic system.

17. The system of claim 16, wherein reconstructing the missing information comprises:
performing Delaunay triangulation on the plurality of fiber core locations to generate triangulation data; and
performing Barycentric interpolation using the triangulation data to produce the missing information.

18. The system of claim 17, wherein determining the plurality of fiber core locations in the image comprises localizing fiber core pixels using a reference image and a two dimensional Gaussian function to model light coming out from each of the plurality of optical fibers.

19. The system of claim 17, wherein determining the plurality of fiber core locations in the image comprises:
performing a first round of fiber core pixel candidate screening using individual threshold values set in accordance with illumination settings of the endoscopic system; and
performing a second round of fiber core pixel candidate screening to remove incorrect core pixels.

20. The system of claim 19, wherein performing the second round of fiber core pixel candidate screening comprises using a mask-based approach to remove incorrect core pixels.

* * * * *

UNITED STATES PATENT AND TRADEMARK OFFICE
CERTIFICATE OF CORRECTION

PATENT NO. : 10,891,730 B1  
APPLICATION NO. : 16/206958  
DATED : January 12, 2021  
INVENTOR(S) : Pu Wang, Francesco Cutrale and Scott E. Fraser Page 1 of 1

It is certified that error appears in the above-identified patent and that said Letters Patent is hereby corrected as shown below:

On the Title Page

Column 2, under Primary Examiner, delete "Uptal" and insert -- Utpal -- therefor.

Signed and Sealed this  
Thirtieth Day of March, 2021

Drew Hirshfeld  
*Performing the Functions and Duties of the*  
*Under Secretary of Commerce for Intellectual Property and*  
*Director of the United States Patent and Trademark Office*